US010815524B2

(12) United States Patent
Nammoku et al.

(10) Patent No.: US 10,815,524 B2
(45) Date of Patent: *Oct. 27, 2020

(54) NUCLEIC ACID ANALYZER

(71) Applicant: Hitachi High-Tech Corporation, Minato-ku, Tokyo (JP)

(72) Inventors: Manami Nammoku, Tokyo (JP); Terumi Tamura, Tokyo (JP); Kohshi Maeda, Tokyo (JP); Daisuke Morishima, Tokyo (JP); Toshinari Sakurai, Tokyo (JP); Wataru Sato, Tokyo (JP)

(73) Assignee: Hitachi High-Tech Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/548,574

(22) PCT Filed: Feb. 23, 2015

(86) PCT No.: PCT/JP2015/054905
§ 371 (c)(1),
(2) Date: Aug. 3, 2017

(87) PCT Pub. No.: WO2016/135798
PCT Pub. Date: Sep. 1, 2016

(65) Prior Publication Data
US 2018/0037930 A1 Feb. 8, 2018

(51) Int. Cl.
*C12Q 1/68* (2018.01)
*C12Q 1/686* (2018.01)
*B01L 7/00* (2006.01)

(52) U.S. Cl.
CPC ............... *C12Q 1/686* (2013.01); *B01L 7/52* (2013.01); *B01L 2200/147* (2013.01); *B01L 2300/0663* (2013.01); *B01L 2300/1822* (2013.01)

(58) Field of Classification Search
CPC .. B01L 7/52; B01L 2200/147; B01L 2300/18; B01L 2300/1822; C12Q 1/686; C12Q 2527/107
See application file for complete search history.

(56) References Cited

U.S. PATENT DOCUMENTS 6,389,225 B1 5/2002 Malinoski et al.
6,509,193 B1 * 1/2003 Tajima .................... B03C 1/288
436/49

(Continued)

FOREIGN PATENT DOCUMENTS

JP 8-117590 A 5/1996
JP 2001-521379 A 11/2001
(Continued)

OTHER PUBLICATIONS

14913809 Certified Copy of Foreign Priority Jun. 19, 2014 (Year: 2014).*

(Continued)

*Primary Examiner* — Betty J Forman
(74) *Attorney, Agent, or Firm* — Crowell & Moring LLP

(57) ABSTRACT

The purpose of the invention is to provide a nucleic acid analyzer that sets and executes temperature regulation, said temperature regulation matching the characteristics of analyzing items and the configuration of the analyzer, by a simple operation while preventing deterioration in analytical performance caused by partial overheating of a liquid reaction mixture to thereby improve temperature change speed and shorten analysis time. To achieve the above purpose, provided is a method wherein, in the case of performing overshooting: as a first processing, the temperature is continuously elevated until reaching a target overshoot temperature; as a second processing, after reaching the aforesaid temperature, the overshoot target temperature is maintained for a preset period of time; and, as a third processing, the (Continued)

temperature is continuously lowered until reaching a target temperature of the liquid reaction mixture. By executing the first to third processings, regulation is conducted so that temperature measurement values are in a trapezoidal form.

5 Claims, 14 Drawing Sheets

(56) References Cited

U.S. PATENT DOCUMENTS

| | | | |
|---|---|---|---|
| 9,347,096 B2* | 5/2016 | Morishima | C12Q 1/686 |
| 9,993,822 B2* | 6/2018 | Sugiyama | B01L 7/52 |
| 2001/0019826 A1 | 9/2001 | Ammann | |
| 2008/0032347 A1* | 2/2008 | Sarofim | B01L 7/52 |
| | | | 435/91.2 |
| 2009/0020427 A1 | 1/2009 | Tan et al. | |
| 2011/0294131 A1* | 12/2011 | Maeda | G01N 35/025 |
| | | | 435/6.12 |
| 2013/0168074 A1* | 7/2013 | Higginbotham | B01L 7/52 |
| | | | 165/287 |
| 2013/0316441 A1* | 11/2013 | Morishima | C12Q 1/686 |
| | | | 435/287.2 |
| 2014/0170734 A1* | 6/2014 | Shoji | B01L 7/52 |
| | | | 435/286.2 |
| 2016/0245690 A1* | 8/2016 | Nammoku | G01N 21/51 |

FOREIGN PATENT DOCUMENTS

| | | |
|---|---|---|
| JP | 2002-513936 A | 5/2002 |
| JP | 2002-520622 A | 7/2002 |
| JP | 2010-523116 A | 7/2010 |
| JP | 2012-100549 A | 5/2012 |
| JP | 2014-131493 A | 7/2014 |
| JP | 2014131493 A * | 7/2014 |
| WO | WO 98/43740 A2 | 10/1998 |

OTHER PUBLICATIONS

M. Hashimoto et al., "Instrumentation of a PLC-Regulated Temperature Cycler with a PID Control Unit and Its Use for Miniaturized PCT Systems with Reduced Volumes of Aqueous Sample Droplets Isolated in Oil Phase in a Microwell," Analytical Sciences, Dec. 2011, pp. 1191-1196, vol. 27, No. 12, The Japan Society for Analytical Chemistry (eight (8) pages).

International Search Report (PCT/ISA/210) issued in PCT Application No. PCT/JP2015/054905 dated Jun. 2, 2015 with English-language translation (nine (9) pages).

Japanese-language Written Opinion (PCT/ISA/237) issued in PCT Application No. PCT/JP2015/054905 dated Jun. 2, 2015 (six (6) pages).

Japanese-language Office Action issued in counterpart Japanese Application No. 2017-501554 dated Sep. 11, 2018 with unverified English translation (nine pages).

* cited by examiner

[Fig. 1A]
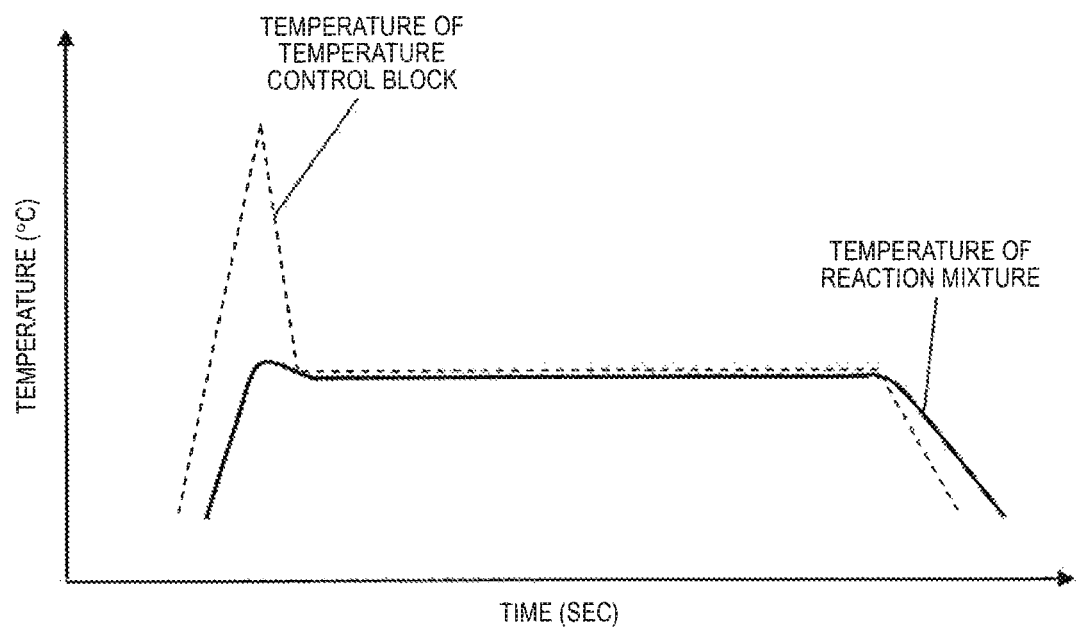
[Fig. 1B]
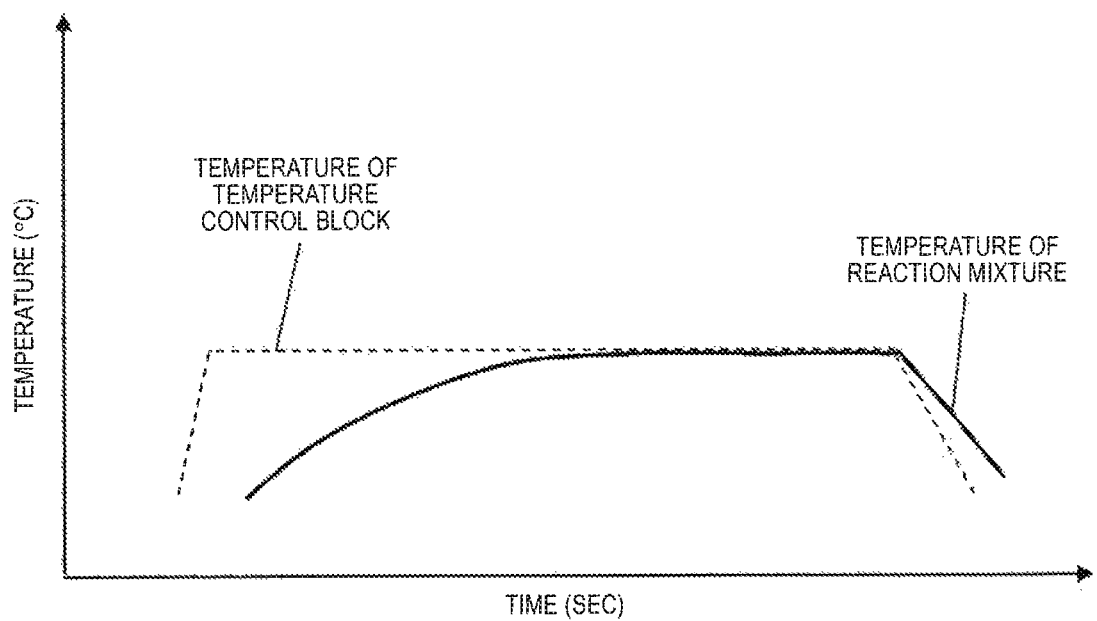

[Fig. 1C]
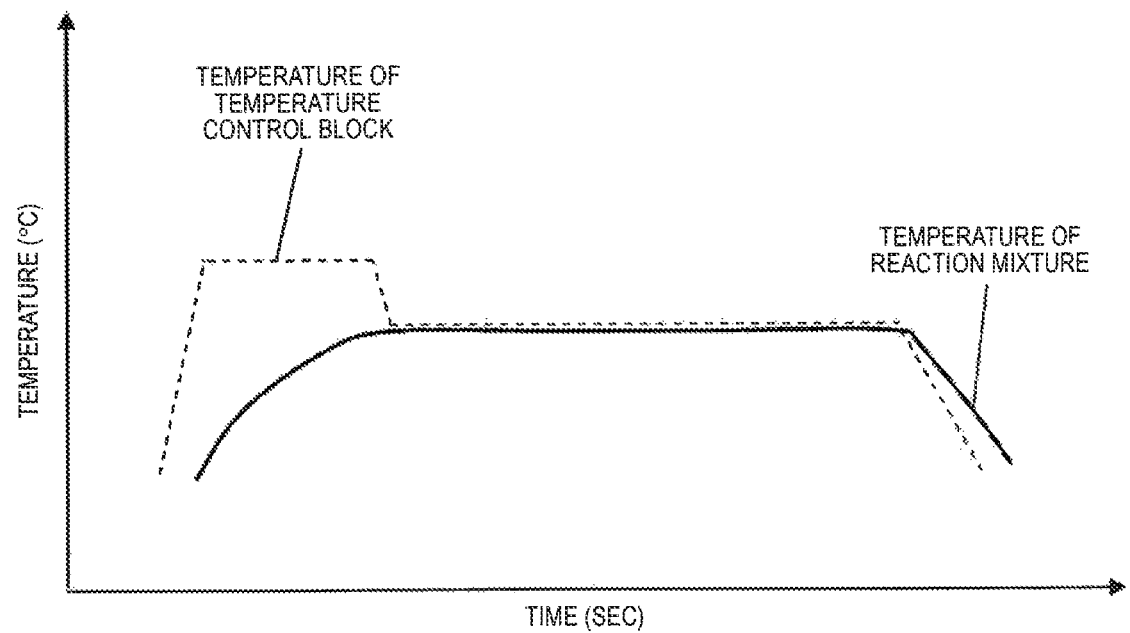

[Fig. 2]
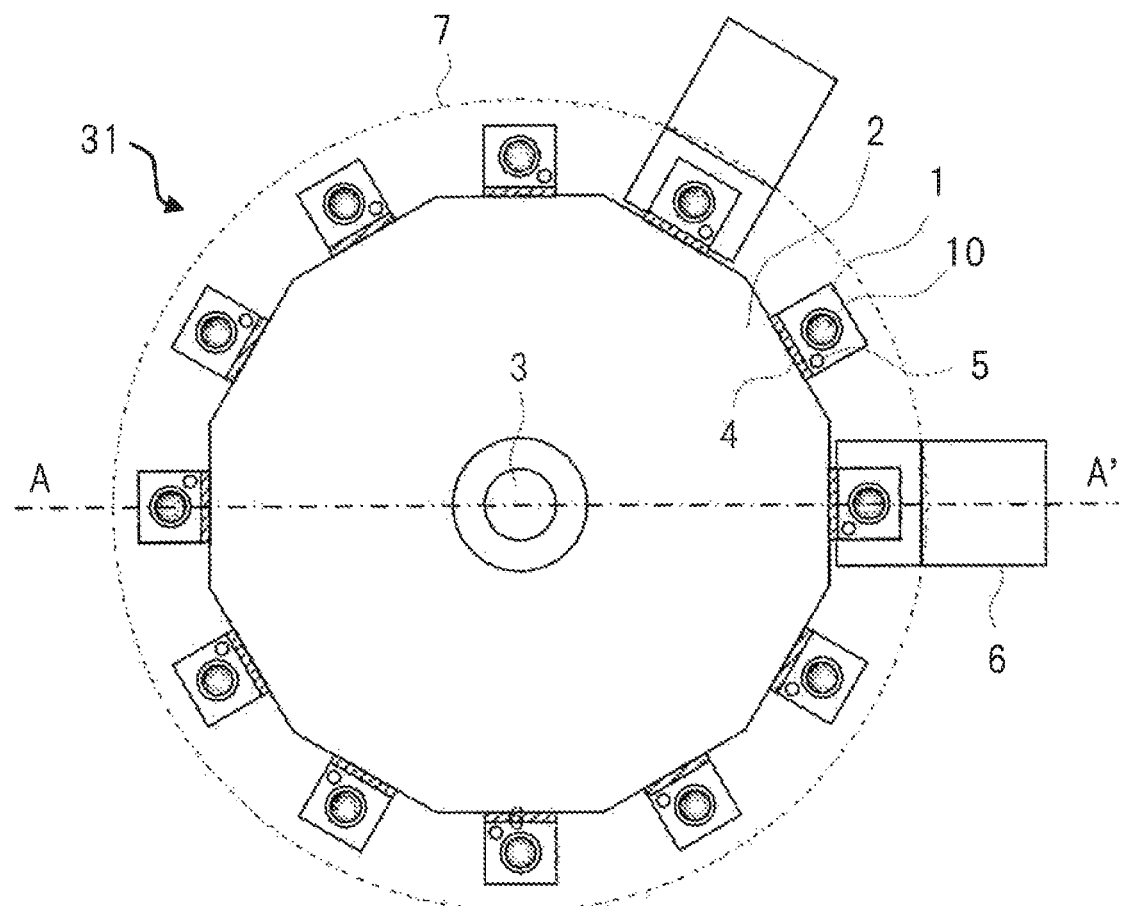

[Fig. 3]
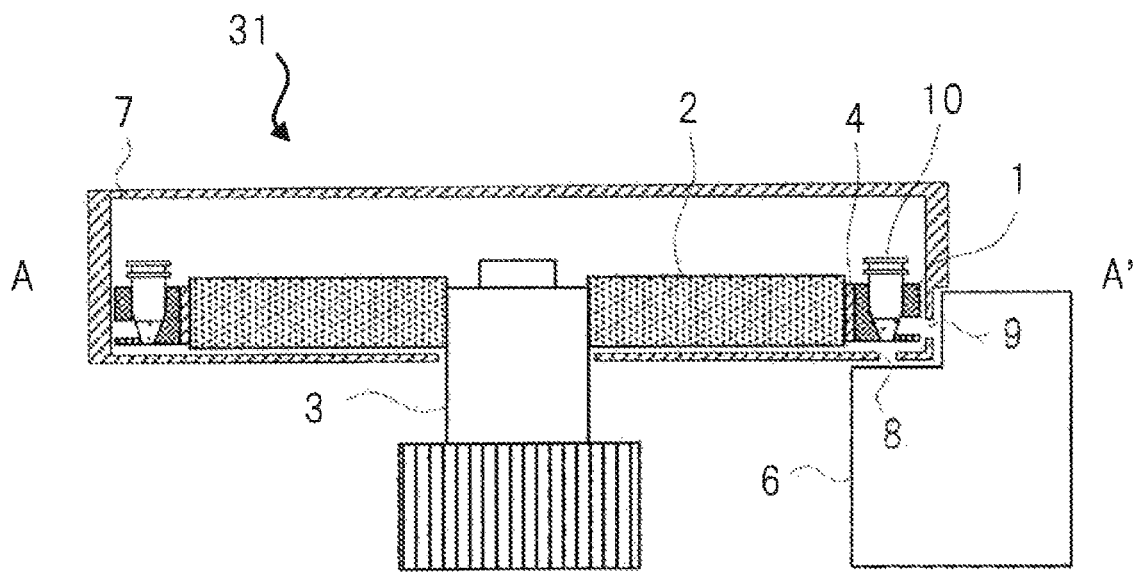
[Fig. 4]
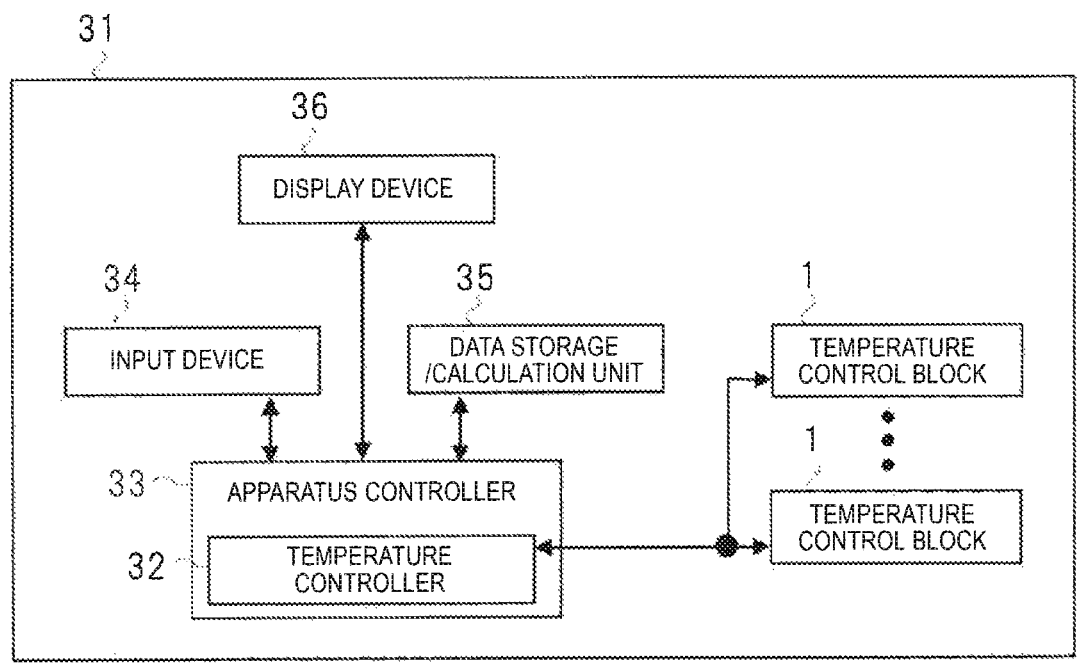

[Fig. 5]
| STAGE No. | STEP No. | TEMPERATURE | TIME | REPEAT COUNT |
|---|---|---|---|---|
| 1 | 1 | 55°C | 120s | 1 |
| | 2 | 95°C | 300s | |
| 2 | 1 | 95°C | 30s | 50 |
| | 2 | 55°C | 60s | |
| | 3 | 72°C | 30s | |
[Fig. 6]
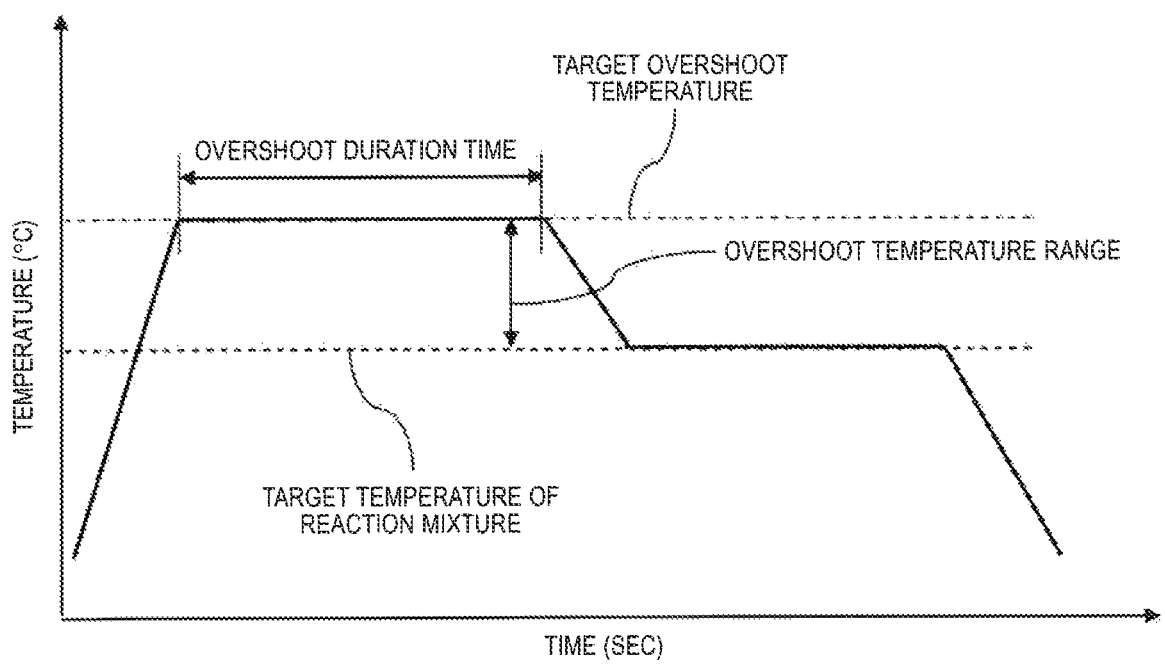

[Fig. 7]
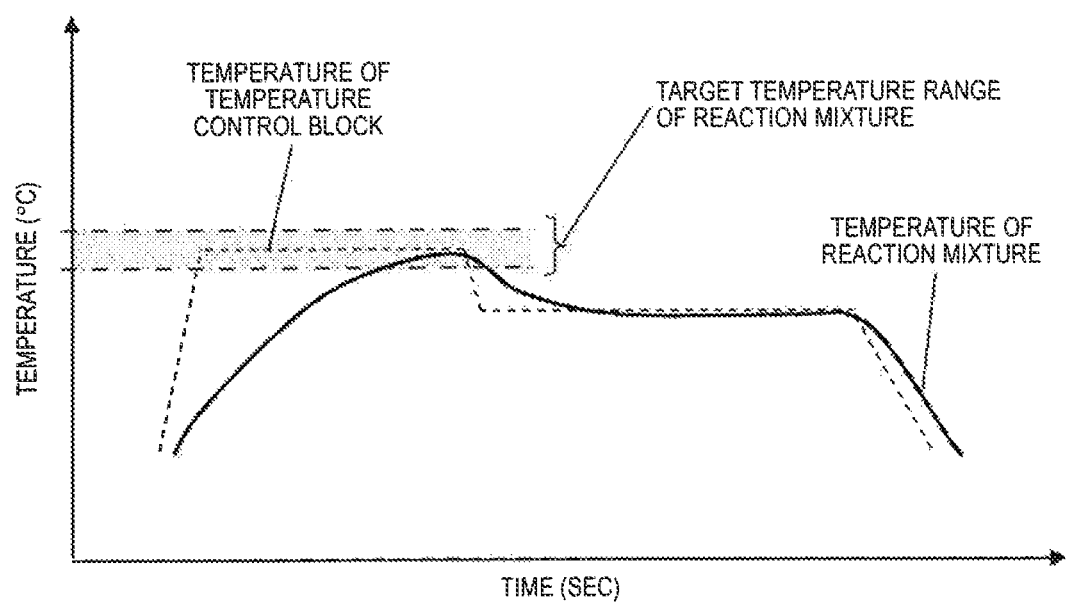

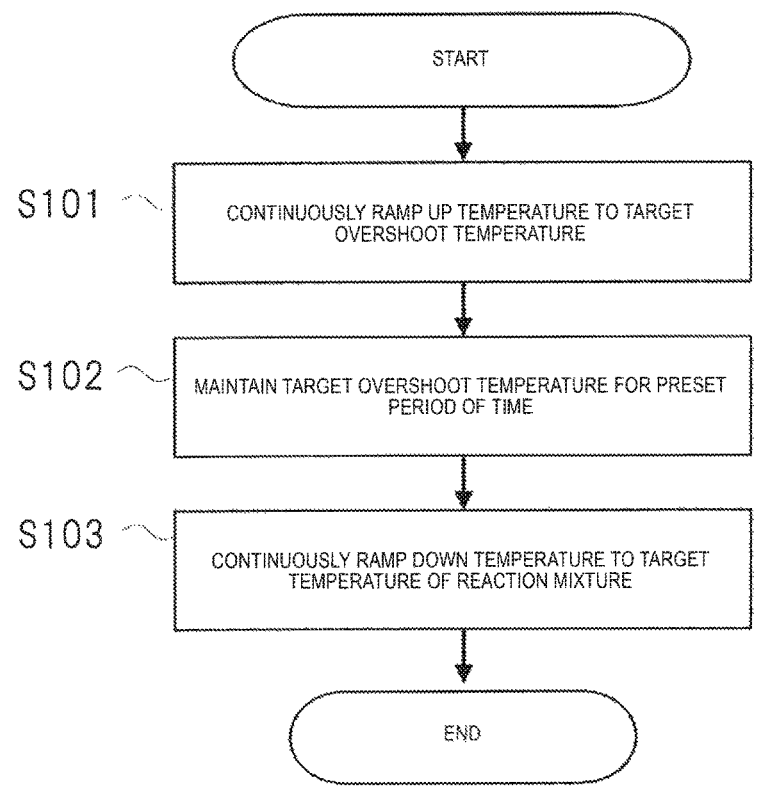
[Fig. 8]

[Fig. 9]
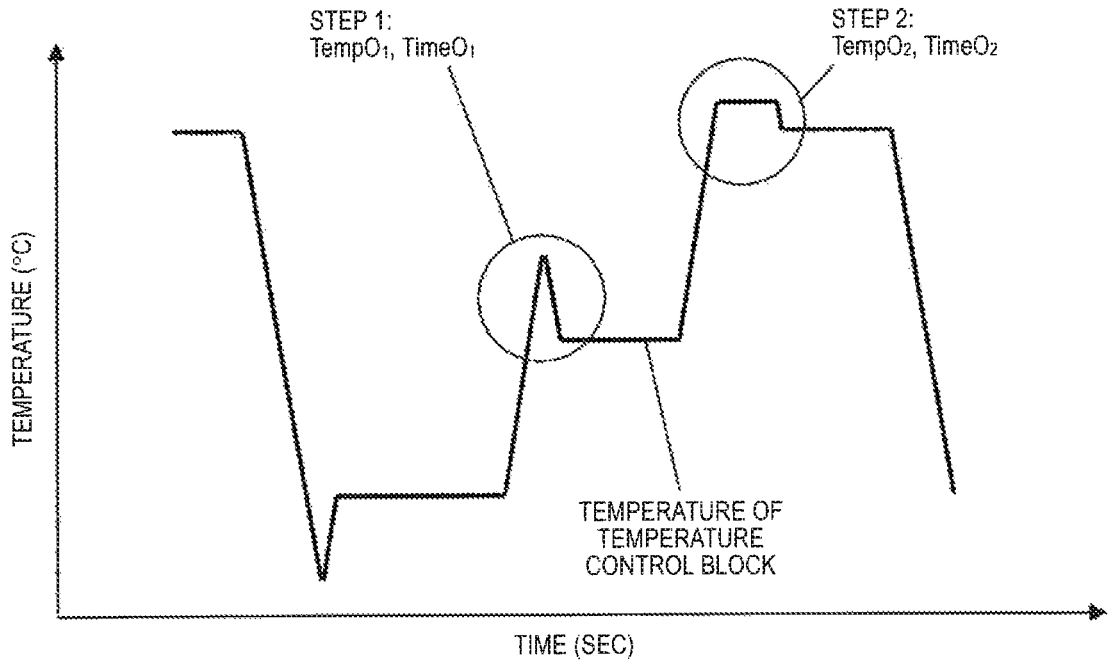
[Fig. 10]
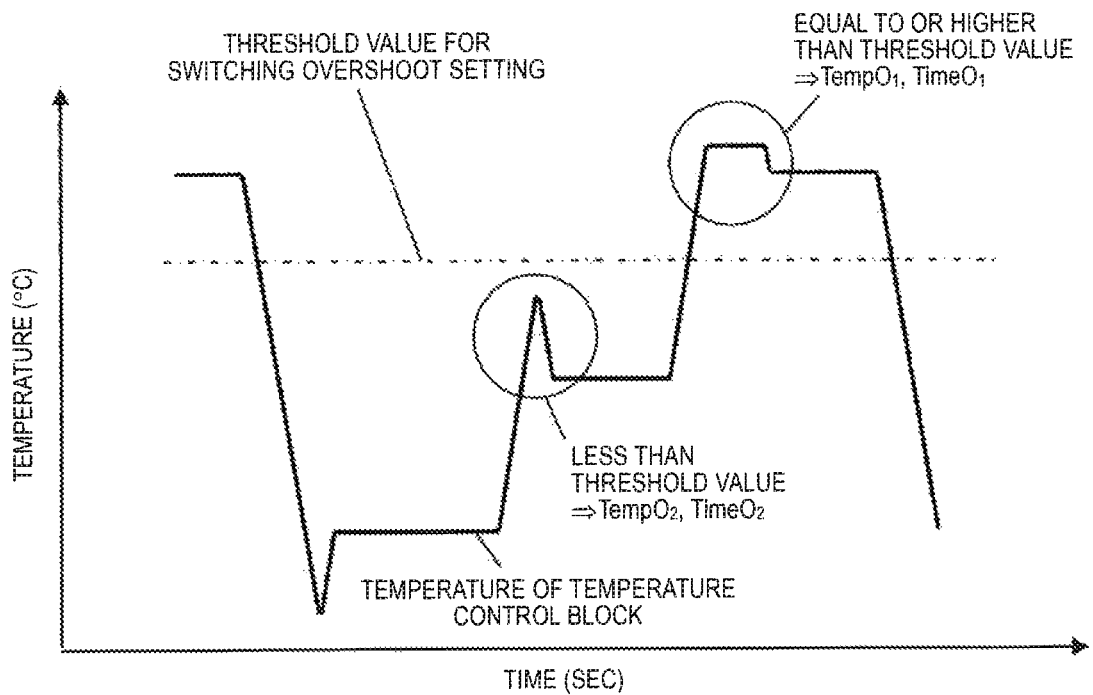

[Fig. 11]
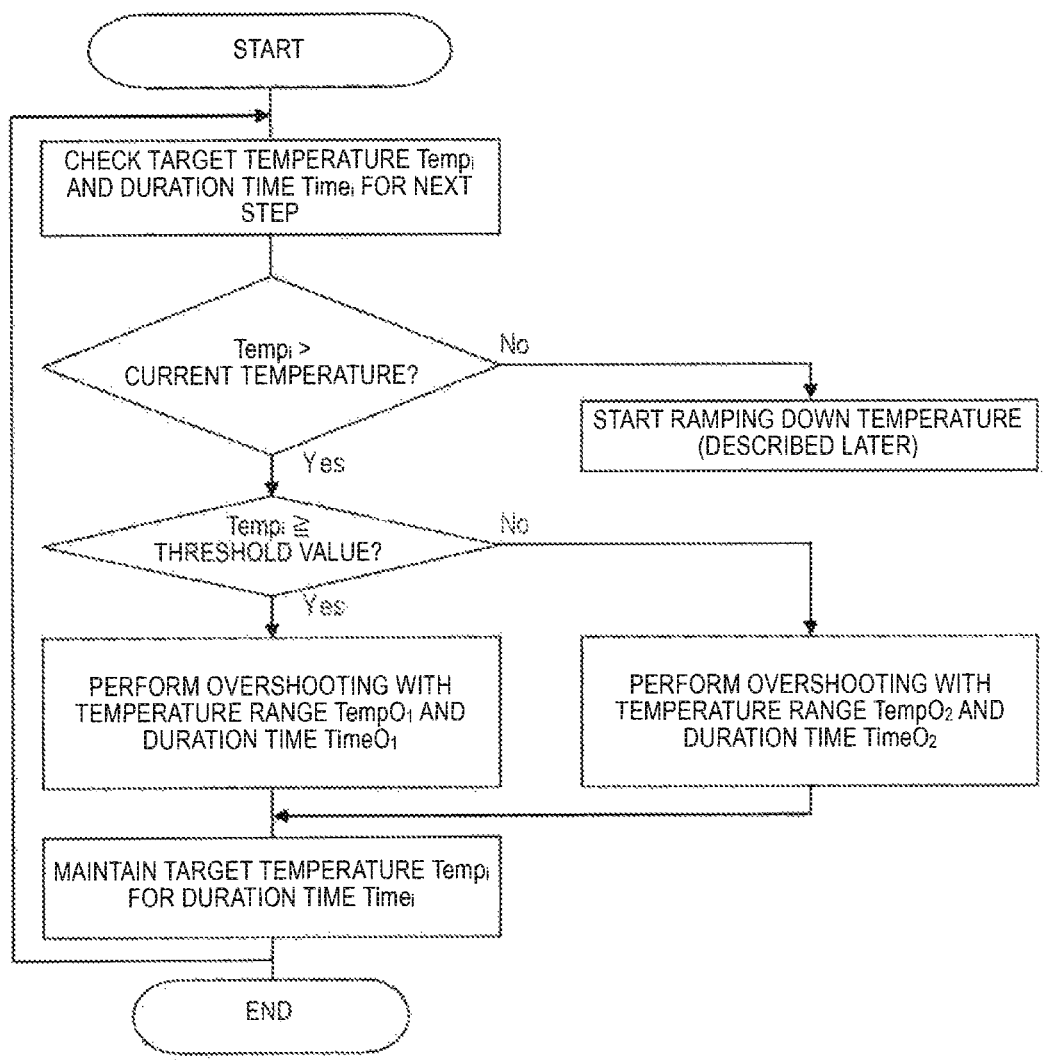

[Fig. 12A]
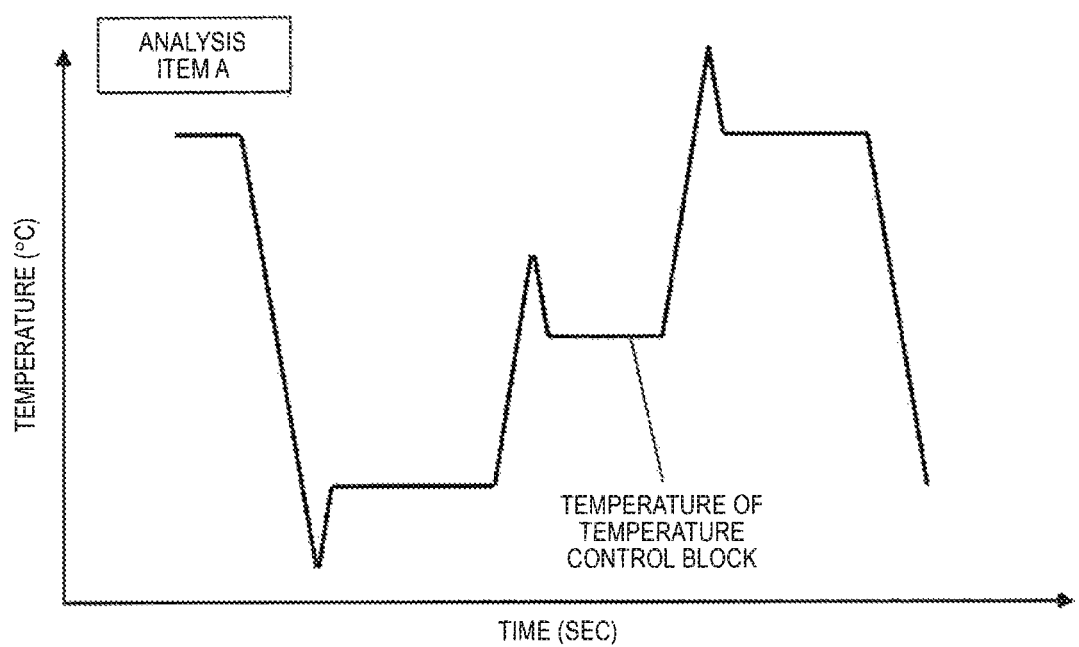
[Fig. 12B]
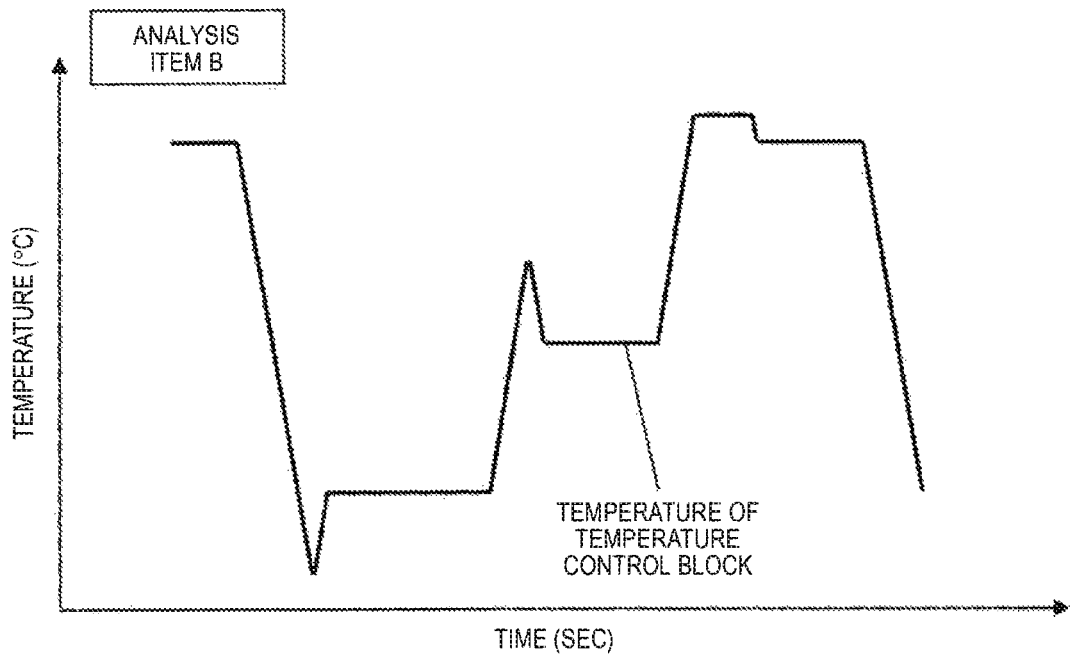

[Fig. 13]
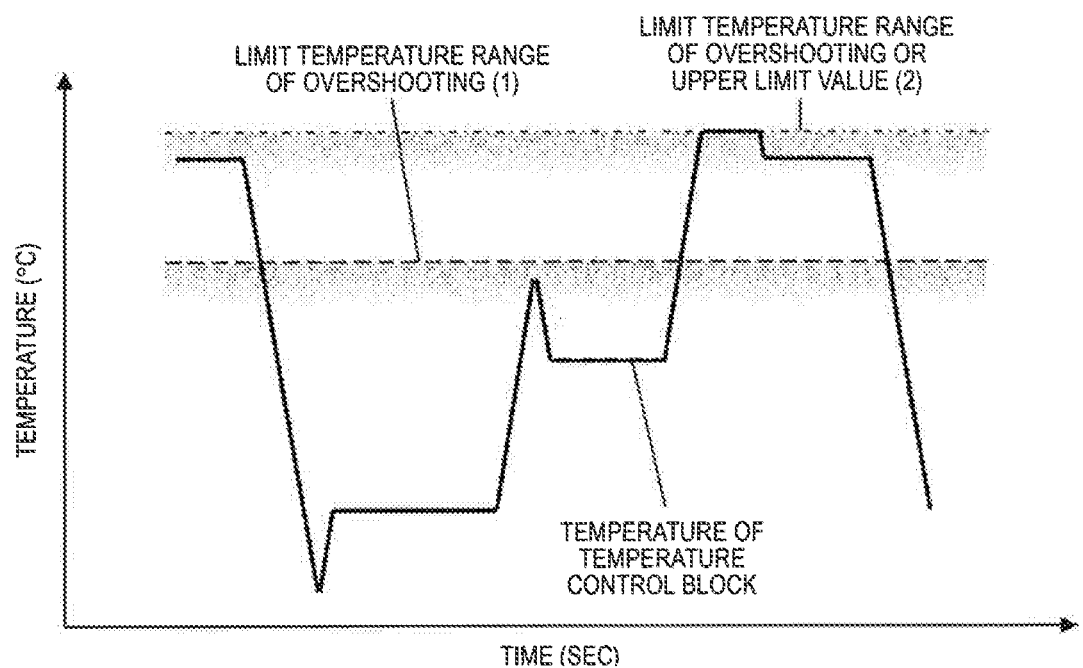

[Fig. 14]
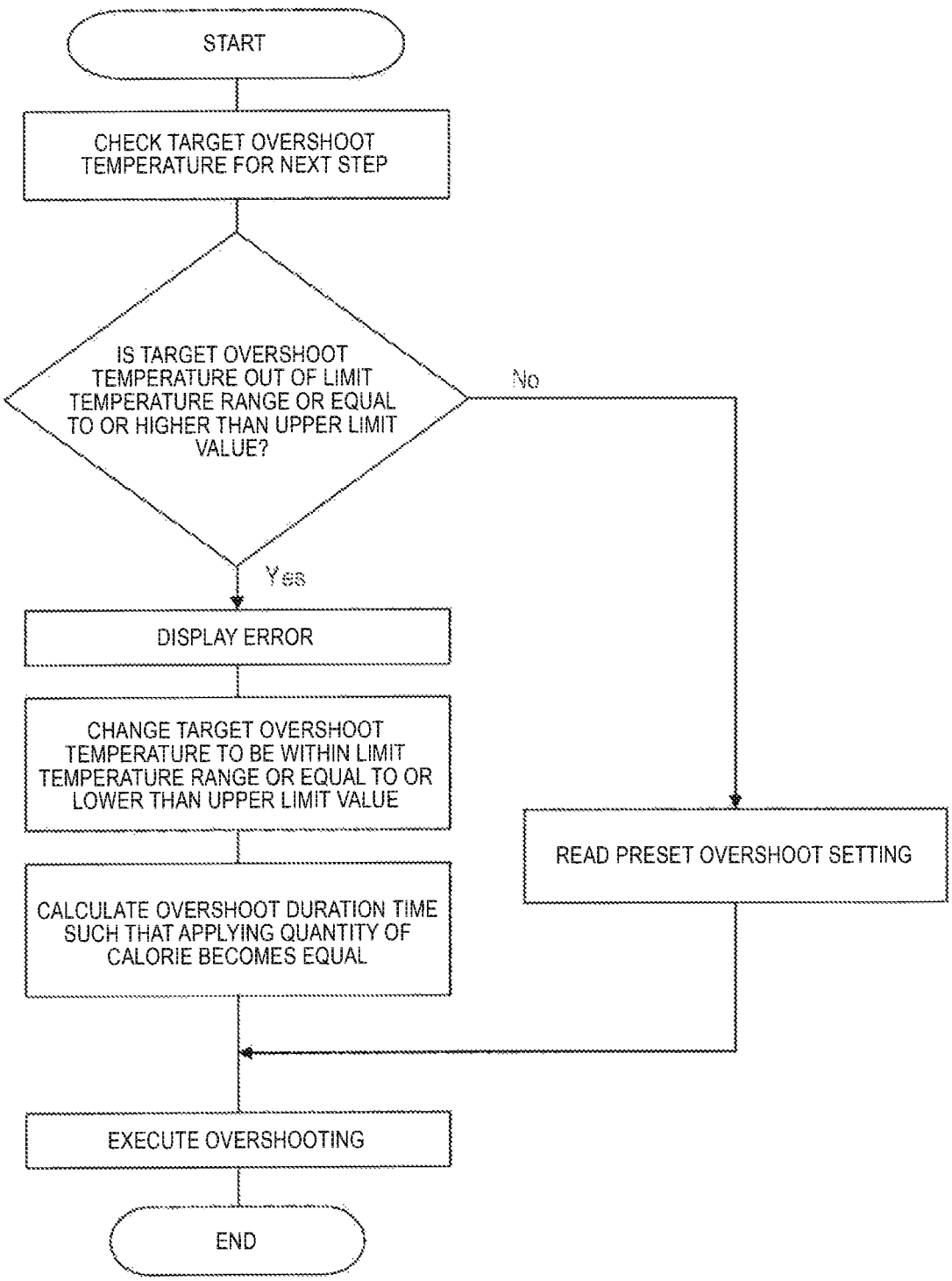

[Fig. 15]
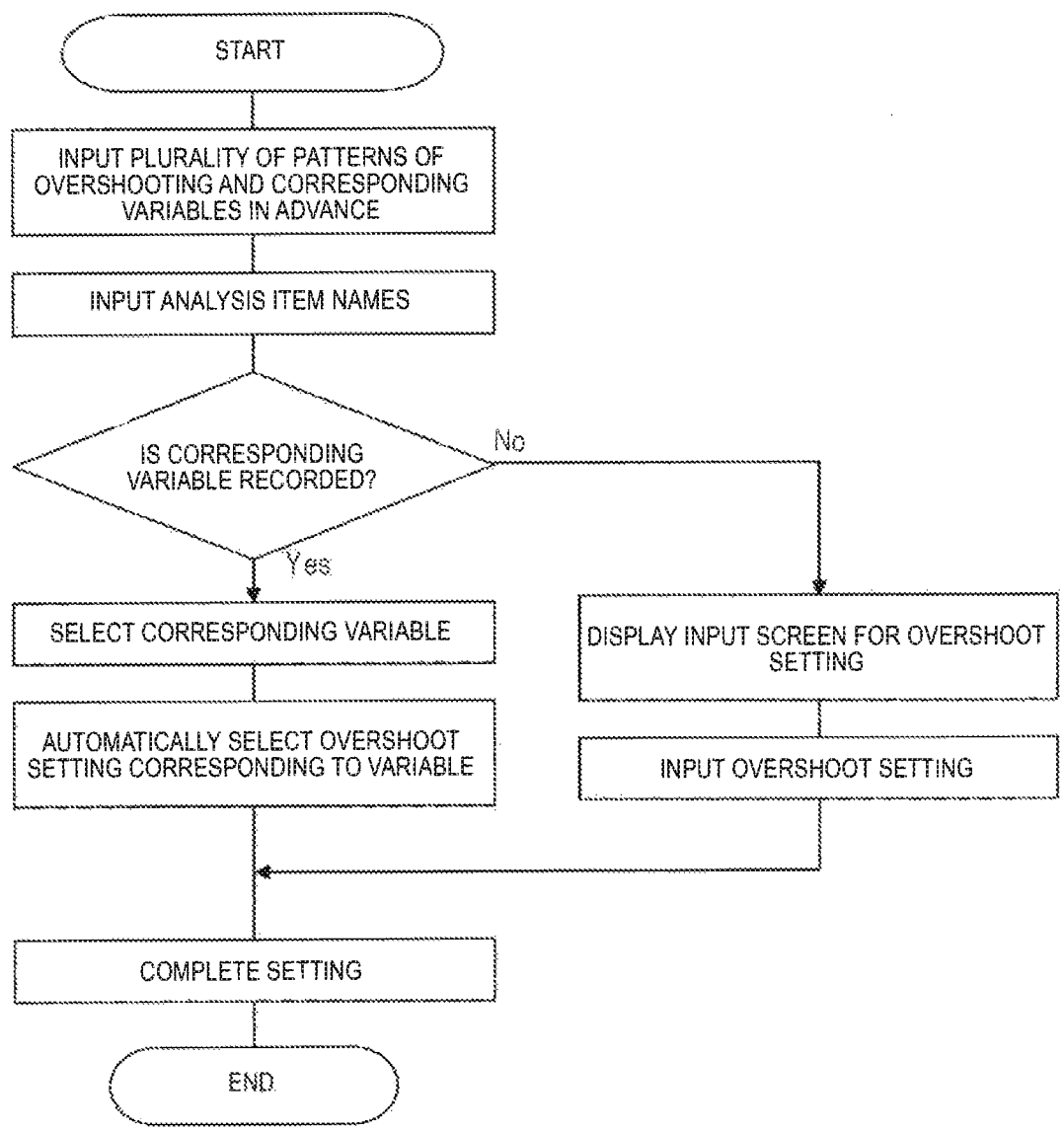

[Fig. 16]
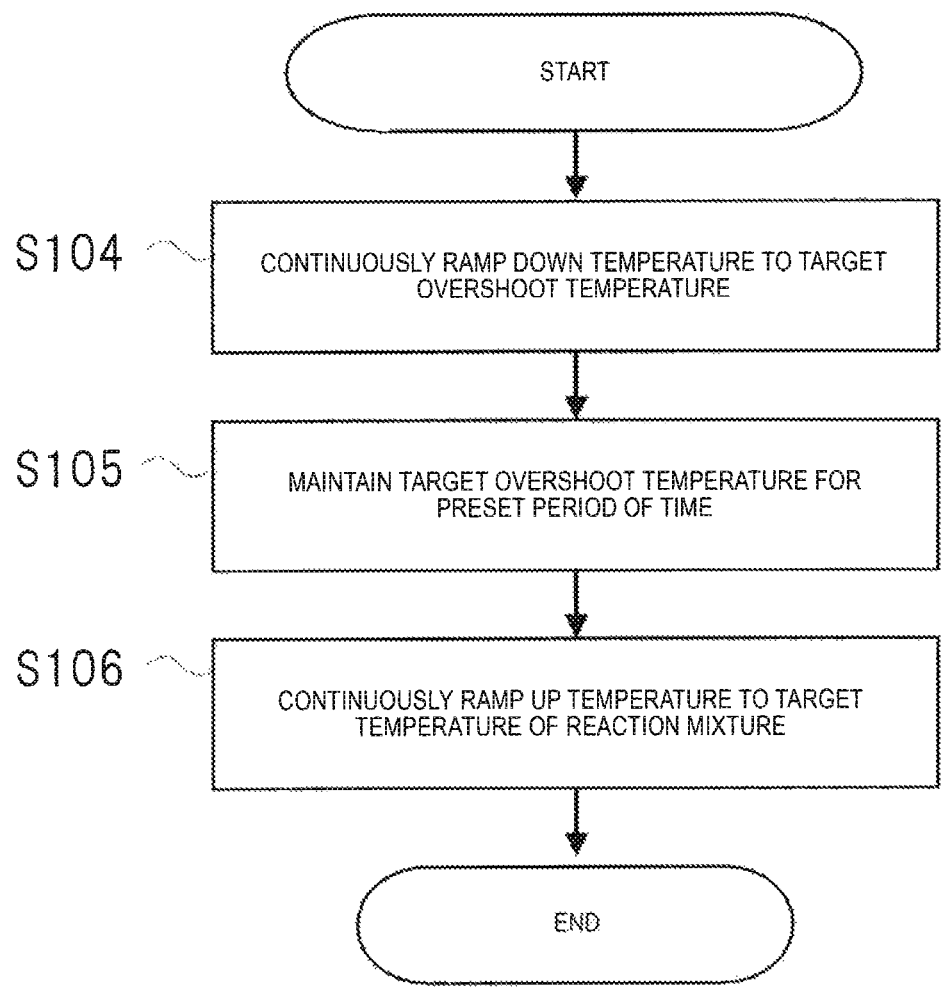

US 10,815,524 B2

NUCLEIC ACID ANALYZER

TECHNICAL FIELD

The present invention relates to a nucleic acid analyzer which analyzes a biological sample by amplifying nucleic acid included in the biological sample.

BACKGROUND ART

Analyses of nucleic acid included in a biological sample such as blood, blood plasma, and a tissue piece are performed not only in academic studies such as biology, biochemistry, and medical science but also in many different fields of industries such as diagnosis, breed improvement of farm products, and food inspection. A method which has most widely spread as a method of analyzing nucleic acid is a technology called polymerase chain reaction (PCR) in which the nucleic acid in a region intended to be analyzed is amplified in a base sequence-specific manner. In the PCR, a reaction mixture including nucleic acid and a reagent for amplifying the nucleic acid is heated to approximately 95° C. for denature, after that, the nucleic acid is cooled to approximately 60° C. for annealing and extension reaction. The temperature shift between 95° C. and 60° C. is repeated 30 times (or more until 40 times). In many cases, means for detecting amplification of the nucleic acid proceeding in accordance with the reaction is performed by mixing a fluorescent labeled compound having fluorescence intensity which varies depending on a PCR product amount into a reaction mixture, irradiating the mixed result with excitation light, and measuring the fluorescence intensity radiated from the fluorescent labeled compound.

Generally, compared to a temperature change of a temperature control block, the temperature change of the reaction mixture (analysis subject) is delayed. Therefore, for the purpose of urging the temperature of the reaction mixture to reach a target temperature, many nucleic acid analyzers perform controlling in which, for example, when the temperature is ramped up, the temperature of the temperature control block is raised to be equal to or higher than the target temperature for the temperature of the reaction mixture and overshooting is performed.

PTL 1 discloses that a temperature control block is used in combination with optimized overshooting which is symmetric in both an up-ramp and a down-ramp, and the most favorable advantage is achieved.

In addition, PTL 2 discloses a random-accessible nucleic acid analyzer employing a configuration in which a reaction vessel is provided with no lid and oil or the like is overlaid in a reaction mixture so as to prevent vaporization.

CITATION LIST

Patent Literature

PTL 1: JP-T-2001-521379
PTL 2: JP-T-2002-513936

SUMMARY OF INVENTION

Technical Problem

However, in the method of PTL 1, since the same overshooting is performed at all times, there are cases of not being able to cope with the difference of a reagent for each analysis item, particularly the characteristics of nucleic acid amplification enzyme.

Actually, in a case where the inventors use a reagent of a certain analysis item, when general spear-type overshooting illustrated in FIG. 1A is employed, a case in which analytical performance deteriorates is checked. When a simulation for finding the reason is performed, it is determined that when the spear-type overshooting is performed at 10° C. in a nucleic acid denaturation step (generally set to 95° C.), 2.9% at the maximum of a reaction mixture exceeds 97° C. In a case of a heat-sensitive nucleic acid amplification enzyme, there is a possibility that most thereof is deactivated while repeating cycles.

Meanwhile, as illustrated in FIG. 1B, in a case of not performing overshooting, since the temperature change of the reaction mixture is delayed compared to a temperature control block, there is a problem in that the temperature of the reaction mixture does not reach a target temperature.

In addition, since water boils at 99.97° C. or higher under 1 atm, in a case of the configuration in PTL 2 in which a reaction vessel has no lid and oil or the like is overlaid in a reaction mixture so as to prevent vaporization, there is a possibility that air bubbles are generated when heating is performed with respect to the nucleic acid denaturation step, and the analytical performance deteriorates.

Moreover, in existing nucleic acid analyzers, setting of an overshoot temperature range or a duration time cannot be changed. Therefore, in every step in any PCR temperature cycle, an analysis is performed with the same setting at all times. In addition, due to a similar reason, in regard to every analysis item, an analysis is performed with the same overshoot setting at all times.

An object of the invention is to provide a nucleic acid analyzer in which while analytical performance is prevented from deteriorating due to partial overheating of a reaction mixture, in order to shorten an analysis time by improving a temperature change speed of the reaction mixture, temperature control matching an analysis item or the characteristics of the configuration of the apparatus is set and executed by performing a simple operation.

Solution to Problem

As an apparatus realizing the invention, there is provided a nucleic acid analyzer including a temperature control unit which controls a temperature of a sample including nucleic acid, and a temperature controller which controls the temperature control unit. The temperature control unit includes a holder which holds a vessel including the sample, a temperature controlling device which controls the temperature of the sample provided in the holder, and a temperature sensor which monitors a temperature of the holder. The temperature controller controls the temperature control unit such that a curve of temperature measurement values for duration time shows a trapezoidal shape.

Advantageous Effects of Invention

By applying the invention, in a nucleic acid denaturation step performed at a high temperature, overheating of the reaction mixture caused due to overshooting is restrained. Therefore, nucleic acid amplification enzyme is prevented from being deactivated, and analytical performance can be retained. In addition, in a case of a configuration in PTL 2 in which a reaction vessel is provided with no lid and oil or the like is overlaid in a reaction mixture so as to prevent vaporization, overheating of the reaction mixture caused due to overshooting is restrained in the nucleic acid denaturation step. Therefore, air bubbles are prevented from being generated, and the analytical performance can be retained.

Moreover, by changing the overshoot setting in one PCR temperature cycle, a temperature change speed of the reaction mixture can be improved and an analysis time can be shortened.

Similarly, in regard to two or more analysis items different from each other, different kinds of the overshoot setting can be input and performed in accordance with the characteristics of a reagent, particularly the thermal tolerance of nucleic acid analysis enzyme.

BRIEF DESCRIPTION OF DRAWINGS

FIG. 1A is a view illustrating an example of a temperature of a temperature control block and a temperature of a reaction mixture in a case of performing general spear-type overshooting.

FIG. 1B is a view illustrating an example of the temperature of the temperature control block and the temperature of the reaction mixture in a case of not performing overshooting.

FIG. 1C is a view illustrating an example of the temperature of the temperature control block and the temperature of the reaction mixture in a case of performing trapezoidal overshooting in which a target overshoot temperature is retained for a preset period of time.

FIG. 2 is a top view illustrating an example of a configuration of a main portion in a nucleic acid analyzer according to Embodiment 1 of the present Example.

FIG. 3 is a cross-sectional view illustrating an example of a configuration between A-A' in FIG. 2.

FIG. 4 is a schematic block diagram illustrating an example of a main configuration on a functional aspect of the nucleic acid analyzer in FIGS. 2 and 3.

FIG. 5 is a table illustrating an example of parameters of a PCR temperature cycle.

FIG. 6 is a view illustrating parameters required in overshoot setting.

FIG. 7 is a view illustrating an example of temperature changes of the reaction mixture and the temperature control block in a case where the temperature of the temperature control block is controlled such that the temperature of the reaction mixture reaches a set target temperature.

FIG. 8 is a flow chart illustrating an example of processing contents in a case where a temperature controller illustrated in FIG. 4 controls overshooting.

FIG. 9 is a view illustrating an example of the PCR temperature cycle in a case where the trapezoidal overshooting and spear-type overshooting are jointly used.

FIG. 10 is a view illustrating an example of the PCR temperature cycle in a case where a threshold value for switching the overshoot setting is provided and the overshoot setting changes.

FIG. 11 is a flow chart illustrating an example of the processing contents in a case where the threshold value for switching the overshoot setting is provided.

FIG. 12A is a view illustrating an example of the PCR temperature cycle in a case where the same spear-type overshoot setting is applied to all steps.

FIG. 12B is a view illustrating an example of the PCR temperature cycle in a case where differently set overshoot setting is applied to each step.

FIG. 13 is a view illustrating an example of the PCR temperature cycle in a case where a limit temperature of overshooting is provided.

FIG. 14 is a flow chart illustrating an example of the processing contents when overshooting is performed in a case where the limit temperature of overshooting is provided.

FIG. 15 is a flow chart illustrating an example of the processing contents in a case where the overshoot setting is automatically selected by an apparatus controller.

FIG. 16 is a flow chart illustrating an example of the processing contents in a case where the temperature controller 32 illustrated in FIG. 4 controls undershooting.

DESCRIPTION OF EMBODIMENT

Hereinafter, a nucleic acid analyzer according to the present Example will be described in detail with reference to the drawings. In Example, a PCR method will be mainly described. However, the present Example can be realized through various methods including constant-temperature amplification methods such as a LAMP method, a NASBA method, and a TRC method, and the difference of an inspection method does not limit the invention proposed in this specification.

(Embodiment 1) [Configuration of Main Portion of Nucleic Acid Analyzer]

FIG. 2 is a top view illustrating an example of a configuration of a main portion in the nucleic acid analyzer according to Embodiment 1 of the present Example. FIG. 3 is a cross-sectional view illustrating an example of a configuration between A-A' in FIG. 2.

A nucleic acid analyzer 31 in FIGS. 2 and 3 is configured to have a temperature control unit, a carousel 2, a photometer 6, and a shielding plate 7.

The temperature control unit is configured to have a temperature control block (holder) 1 for holding a tube (reaction vessel) with a reaction mixture including nucleic acid, a Peltier device (temperature controlling device) 4 which controls a temperature of the temperature control block 1, and a temperature sensor 5 which monitors the temperature of the temperature control block 1. A plurality of the temperature control blocks 1 (in this example, 12) are disposed around a central axis of the carousel 2 along the outer circumference and are rotatively driven about a rotary axis 3. The Peltier devices 4 are respectively disposed between the plurality of temperature control blocks 1 and the carousel 2. The temperature of the temperature control block 1 is controlled by controlling the Peltier device 4 while monitoring the temperature through the temperature sensor 5 mounted inside the temperature control block 1. The temperatures of the plurality of temperature control blocks 1 can be independently controlled by correspondingly disposing a set of the Peltier device 4 and the temperature sensor 5 for each of the plurality of temperature control blocks 1.

If temperature control for PCR can be performed through a different method, any temperature controlling method may be adopted. For example, it is possible to use an air incubator-type method in which temperature is controlled by changing the temperature of air.

In the outer circumference of the carousel 2, the photometer 6 is disposed. Here, as an example, two photometers 6 respectively using rays of light different from each other in wavelength are illustrated. However, as long as the wavelength from the reaction mixture inside the reaction vessel in the outer circumference, the inner circumference, or the like of the carousel 2 can be detected, one, three, or more photometers 6 may be disposed. Since all of the temperature control blocks 1 are rotatively driven and move on the same circumference, relative positions between the photometer 6 and the temperature control block 1 when passing through in front of the photometer 6 are the same as each other in all of the temperature control blocks 1.

In order to reduce optical noise in a case of an analysis performed by the photometer 6, the plurality of temperature control blocks 1 are covered with the shielding plate 7 including the carousel 2. When an analysis is performed, a tube (reaction vessel) 10 including the reaction mixture (sample) obtained by mixing a reagent or the like into the nucleic acid is held by the temperature control block (holder) 1. All of the temperature control blocks 1 are individually provided with a window 8 for irradiation of excitation light, the window for receiving excitation light from the photometer 6, and a window 9 for detection of fluorescent light, the window through which the photometer 1 receives in fluorescent light. Here, the window 8 for irradiation of excitation light is disposed on a lower surface side of the temperature control block 1 and the window 9 for detection of fluorescent light is disposed on a side surface side of the temperature control block 1. However, disposition of the windows can be freely set in accordance with the structure of the photometer.

Subsequently, in regard to the nucleic acid analyzer configured as described above, a method of controlling the apparatus for performing trapezoidal overshooting will be described. As the method of controlling the apparatus for performing the trapezoidal overshooting, through the following three phases of processing, overshooting of the temperature of the temperature control unit holding the reaction mixture is performed as illustrated in FIG. 1C.

As first processing, the temperature control unit continuously ramps up the temperature until the temperature reaches a target overshoot temperature. As second processing, the temperature control unit holds the target overshoot temperature for a preset period of time after reaching the temperature. As third processing, the temperature control unit continuously ramps down the temperature until the temperature reaches a target temperature of the reaction mixture. By performing the first processing to the third processing, the temperature control unit conducts controlling such that a curve of temperature measurement values shows a trapezoidal waveform. At this time, it is desirable that each of the first processing of ramping up the temperature and the third processing of ramping down the temperature has a constant ramp rate.

For each preset temperature in a PCR temperature cycle, overshoot setting, that is, the target temperature and the duration time of overshooting may be changed. In addition, patterns of overshoot setting different from each other may be executed in regard to two or more analysis items different from each other. Moreover, it is desirable that the overshoot setting is directly input or is input from the outside via a USB, a bar code, a network or the like.

FIG. 4 is a schematic block diagram illustrating an example of a main configuration on a functional aspect of the nucleic acid analyzer in FIGS. 2 and 3. The nucleic acid analyzer 31 illustrated in FIG. 4 includes a temperature controller 32 which controls the temperatures thereof, in addition to the plurality of temperature control blocks 1 described above. The temperature controller 32 is a part of an apparatus controller 33 which plays a role of controlling the nucleic acid analyzer. The temperature controller 32 is mainly configured to be a computer system or like and controls the temperature of each of the temperature control block 1 based on a preset processing sequence.

An input device 34 receives an input of information from the outside with respect to the nucleic acid analyzer. As a method of inputting information, information may be input through a file form via a bar code and a USB and may be input via a network, in addition to being directly input via a keyboard or the like.

A data storage/calculation unit 35 records information input via the input device 34. As necessary, the data storage/calculation unit 35 transmits the information to the apparatus controller 33. In addition, in regard to the temperature control, the data storage/calculation unit 35 records parameters of the PCR temperature cycle and the overshoot setting and performs calculation required in the temperature control.

A display device 36 displays information such as a state of the apparatus including an alarm, an analysis result, and an input screen for variables required in the controlling.

[Temperature Controlling Method]

Subsequently, parameters for performing the PCR temperature cycle by using the nucleic acid analyzer of the present Example will be described.

FIG. 5 illustrates an example of the parameters of the PCR temperature cycle. The parameters of the temperature cycle are broadly divided into stages. In this example, there are two stages. However, there may be one stage or three or more stages. A repeat count of the stage is set to each of the stages.

Each of the stages is configured to include one step or two or more steps. A combination of a temperature and a duration time is set for each step. When an analysis starts, the temperature of the temperature control block 1 is controlled by the temperature controller 32 so as to be changed in order from Step 1 of Stage 1.

Depending on the configuration of the nucleic acid analyzer, there are cases where the target temperature of the reaction mixture and the target temperature of the temperature control block 1 for causing the reaction mixture to reach the target temperature are not the same as each other. Therefore, the temperature of the temperature control block 1 may be controlled to be a temperature which is calculated based on the target temperature of the reaction mixture by using a correction formula set in advance.

[Overshoot Controlling Method]

Subsequently, a method of controlling overshooting performed by the nucleic acid analyzer of the present Example, and the overshoot setting will be described. The method of controlling overshooting described in the present Example is a method in which the temperature controller 32 controls the Peltier device (temperature controlling device) 4 controlling the temperature of the temperature control block 1.

FIG. 6 is a view illustrating parameters required in overshoot setting. In the present Example, the overshoot setting is configured to include two factors of an overshoot temperature range and the overshoot duration time for retaining the target overshoot temperature. The target overshoot temperature is obtained by the sum of the target temperature of the reaction mixture for the next step and the overshoot temperature range.

In the present Example, overshooting is performed for the purpose of urging the temperature of the reaction mixture to reach the target temperature for the next step and is defined as controlling the temperature of the temperature control block 1 to be the original target temperature or higher.

FIG. 7 is a view illustrating an example of temperature changes of the reaction mixture inside the tube 10 and the temperature control block 1 in a case where the temperature of the temperature control block 1 is controlled by the temperature controller 32 such that the temperature of the reaction mixture inside the tube 1 reaches the target temperature of the reaction mixture set in advance. In the present Example, in a case where the temperature of the reaction mixture reaches the set target temperature or a target temperature range set based on the target temperature, controlling performed at that time is considered as a step in the PCR temperature cycle instead of the controlling of overshooting. At this time, the target temperature range is the same as the temperature range used for determining that the temperature reaches the target temperature through ordinary temperature control.

Meanwhile, in a case where controlling of the target temperature for the next step starts while the temperature of the reaction mixture does not reach the set target temperature, the controlling is determined to be overshooting instead of a step in the independent PCR temperature cycle.

FIG. 8 is a flow chart illustrating an example of processing contents in a case where the temperature controller 32 illustrated in FIG. 4 controls overshooting. Through the following three phases of processing, overshooting of the temperature of the temperature control unit holding the reaction mixture is performed as illustrated in FIG. 1C.

As the first processing, the temperature control unit continuously ramps up the temperature until the temperature reaches the target overshoot temperature (Step S101). As the second processing holding the target overshoot temperature for a preset period of time after reaching the temperature (Step S102) with temperature control unit. As the third processing, the temperature control unit continuously ramps down the temperature until the temperature reaches the target temperature of the reaction mixture (Step S103).

By performing the first processing to the third processing, the temperature control unit conducts controlling such that a curve of temperature measurement values shows a trapezoidal waveform. At this time, it is desirable that each of the first processing of ramping up the temperature and the third processing of ramping down the temperature has a constant ramp rate at all times.

As described above, in a nucleic acid denaturation step performed at a high temperature, overheating of the reaction mixture caused due to overshooting is restrained. Therefore, nucleic acid amplification enzyme is prevented from being deactivated, and analytical performance can be retained. In addition, in a case of a configuration in which the reaction vessel is provided with no lid and oil or the like is overlaid in a reaction mixture so as to prevent vaporization, in the nucleic acid denaturation step, overheating of the reaction mixture caused due to overshooting is restrained. Therefore, air bubbles are prevented from being generated, and the analytical performance can be retained.

In the present Example, in the second processing, overshooting including the processing of retaining the target overshoot temperature will be referred to as trapezoidal overshooting. Moreover, general overshooting which starts ramping down the temperature without performing the processing of retaining the temperature, after reaching the target temperature will be referred to as spear-type overshooting. That is, the spear-type overshooting is also performed in a case where the duration time at the target overshoot temperature is zero in Step S102 of the flowchart illustrated in FIG. 8.

FIG. 9 is a view illustrating an example of the PCR temperature cycle in a case where the trapezoidal overshooting and the spear-type overshooting are jointly used. In this manner, in each step, the overshoot setting, that is, the overshoot temperature and the overshoot duration time may be differently set. For example, with respect to overshooting for deactivated nucleic acid amplification enzyme or the nucleic acid denaturation step which greatly affects air bubbles generated inside the reaction mixture, trapezoidal overshoot setting having a small temperature range may be applied. Meanwhile, with respect to overshooting for a nucleic acid elongation step which affects air bubbles thereof a little, general spear-type overshooting setting may be applied in order to improve a temperature change speed of the reaction mixture.

As described above, by jointly using a plurality of kinds of overshoot setting different from each other in one PCR temperature cycle, while overheating of the reaction mixture is prevented, the temperature change speed of the reaction mixture can be improved when a temperature change is performed with respect to the step having a small influence of overheating, and the analysis time can be shortened.

FIG. 10 is a view illustrating an example of the PCR temperature cycle in a case where a threshold value for switching the overshoot setting is provided and the overshoot setting changes. In this manner, the threshold value for switching the overshoot setting may be provided such that different kinds of overshoot setting are respectively applied to a case where the target temperature is equal to or higher than the threshold value and a case where the target temperature is less than the threshold value. In FIG. 10, controlling is conducted by the temperature controller 32 such that the spear-type overshooting is executed in a case of being less than the threshold value and the trapezoidal overshooting is executed in a case of being equal to or higher than the threshold value.

FIG. 11 is a flow chart illustrating an example of the processing contents in a case where the threshold value for switching the overshoot setting is provided. In a preparation stage of an analysis, the PCR temperature cycle, the overshoot setting, and the threshold value for switching the setting are set in advance. When the analysis starts, the temperature controller 32 checks a target temperature $Temp_i$ and a duration time $Time_i$ for the next step. In a case where the $Temp_i$ is lower than the current temperature, ramping down the temperature starts. The temperature controlling method of when ramping down the temperature will be described later. In a case where the $Temp_i$ is higher than the current temperature, the $Temp_i$ and the threshold value for switching the overshoot setting are further compared. In a case where the $Temp_i$ is equal to or higher than the threshold value, overshoot setting having corresponding temperature range $TempO_1$ and duration time $TimeO_1$ is applied thereto and is performed. In a case where the $Temp_i$ is less than the threshold value, overshoot setting having corresponding temperature range $TempO_2$ and duration time $TimeO_2$ is applied thereto and is performed. In a case of the spear-type overshooting, the duration time TimeO2 becomes zero. Thereafter, the temperature is ramped down to the target temperature $Temp_i$ set in the PCR temperature cycle, and the temperature is held during the duration time $Time_i$. The above-described processing is repeated until the temperature control set in the PCR temperature cycle ends. At this time, all of the plurality of kinds of overshoot setting may be the trapezoidal overshooting.

Such processing of determining the overshoot setting to be applied to each step may be performed in a stage in which the PCR temperature cycle is set, before an analysis starts.

Accordingly, in accordance with the target temperature for each step in the PCR temperature cycle, the overshoot setting can be simply changed. For example, even though the same nucleic acid amplification enzyme is used, in a case where there are a plurality of analysis items of which the PCR temperature cycles are different from each other, corresponding overshoot setting can be applied by providing one set of overshoot setting and a threshold value for switching the setting.

In addition, at this time, two or more threshold values for switching the overshoot setting may be set in accordance with the number of kinds of the overshoot setting. Accordingly, in accordance with the target temperature for each step in the PCR temperature cycle, the overshoot setting can be minutely set.

In the present Example, a combination of the plurality of kinds of overshoot setting different from each other and the threshold value for switching the overshoot setting is referred to as a pattern of the overshoot setting. It is favorable for the pattern of the overshoot setting to include one kind of the overshoot setting at least. In this case, the threshold value for switching the overshoot setting does not have to be included.

FIG. 12 is a view illustrating an example of the PCR temperature cycle in a case where different patterns of the overshoot setting are applied in regard to analysis items different from each other. FIG. 12A is a view illustrating an example of the PCR temperature cycle in a case where the same spear-type overshoot setting is applied to all steps. For example, in a case of an analytical reagent which includes nucleic acid amplification enzyme having high thermal tolerance, the temperature change speed of the reaction mixture can be improved by applying such setting.

FIG. 12B is a view illustrating an example of the PCR temperature cycle in a case where differently set overshoot setting is applied to each step. For example, in a case of an analytical reagent which includes nucleic acid amplification enzyme having low thermal tolerance, when the temperature is ramped up for the nucleic acid denaturation step, the trapezoidal overshoot setting is applied. When the temperature is ramped up for the nucleic acid elongation step, the spear-type overshooting setting is applied. According to such setting, the reaction mixture can be restrained from being excessively heated, and the nucleic acid amplification enzyme can be prevented from being deactivated in the nucleic acid denaturation step.

FIG. 13 is a view illustrating an example of the PCR temperature cycle in a case where a limit temperature range of overshooting or an upper limit value is provided. In addition to setting the limit temperature range of overshooting and the duration time, the limit temperature range of overshooting is provided. For example, the limit temperature range of overshooting may be determined based on a limit temperature at which the nucleic acid amplification enzyme is deactivated in the nucleic acid denaturation step. In addition, the limit temperature range of overshooting or the upper limit value may be determined based on a limit temperature at which reaction normally proceeds in a step other than the nucleic acid denaturation step.

FIG. 14 is a flow chart illustrating an example of the processing contents when overshooting is performed in a case where the limit temperature range of overshooting or the upper limit value is provided. When overshooting is performed, first, the target overshoot temperature for the next step is calculated and is compared to the limit temperature range of overshooting or the upper limit value. In a case where the target overshoot temperature is within the limit temperature range of overshooting or equal to or lower than the upper limit value, the overshoot setting having the temperature range and the duration time as set in advance is applied and performed. Meanwhile, in a case where the target overshoot temperature is out of the limit temperature range of overshooting or equal to or higher than the upper limit value, the target overshoot temperature is changed so as to be within the limit temperature of overshooting, and a duration time is calculated at that time so as to obtain a quantity of calorie equal to that before the change, thereby performing the overshooting. In addition, in a case where the target overshoot temperature is out of the limit temperature range of overshooting or equal to or higher than the upper limit value, the display device 36 may display an error. As the display device 36 displays the error, a user can be informed of the current overshoot setting.

Such processing of determining the overshoot setting to be applied to each step may be performed in a stage in which the PCR temperature cycle is set, before an analysis starts.

Accordingly, in a case where overheating of the reaction mixture can be caused, while the overheating is prevented, it is possible to apply the overshoot setting for improving the temperature change speed of the reaction mixture as much as possible.

As a component for a pattern of the overshoot setting described above, in addition to the overshoot setting and the threshold value for switching the overshoot setting, the limit temperature range of overshooting or the upper limit value may be included.

The pattern of the overshoot setting is input by a user via the input device 34. As a changing method, in addition to direct inputting, it is desirable to be able to be input via a USB, a bar code, or a network. The pattern of the overshoot setting input via the input device 34 is recorded in the data storage/calculation unit 35. In addition, selection may be made by a user from the patterns of the overshoot setting recorded in the data storage/calculation unit 35 in advance. Accordingly, a user can freely change the pattern of the overshoot setting in accordance with the analysis items.

FIG. 15 is a flow chart illustrating an example of the processing contents in a case where the overshoot setting is automatically selected by the apparatus controller 33. The patterns of the overshoot setting are input to the data storage/calculation unit 35 in advance, and the different variables are respectively applied thereto. In the preparation stage of an analysis, when an analysis item name is input by a user via the input device 34, in a case where a variable corresponding to the analysis item is recorded, the corresponding variable is selected in accordance with the record, and the pattern of the overshoot setting is selected. Meanwhile, in a case where a variable corresponding to the analysis item is not recorded, the input screen for the pattern of the overshoot setting is displayed, and the user is required to make an input.

In addition, in a case where the nucleic acid analyzer 31 has a reagent mixing unit, when a bottle including the analytical reagent is installed in the nucleic acid analyzer 31, the analysis item name embedded in a bar code or the like pasted on the bottle may be read via the input device 34 and the pattern of the overshoot setting may be automatically selected. Moreover, information input via the input device 34 may be a variable and the like other than the analysis item name.

Accordingly, the pattern of the overshoot setting can be automatically changed in accordance with the analysis items.

[Undershooting Controlling Method]

Hereinbefore, the method of changing the overshoot setting has been described. Similarly, in a case of performing undershooting when the temperature is ramped down, as undershoot setting, two parameters of an undershoot temperature range and an undershoot duration time are provided. A target temperature of undershooting is obtained by the difference between the target temperature of the reaction mixture for the next step and the undershoot temperature range.

FIG. 16 is a flow chart illustrating an example of the processing contents in a case where the temperature controller 32 illustrated in FIG. 4 controls undershooting.

As first processing, the temperature control unit continuously ramps down the temperature until the temperature reaches a target undershoot temperature (Step S104).

As second processing, the temperature control unit holds a target undershoot temperature for a preset period of time after reaching the temperature (Step S105).

As third processing, the temperature control unit continuously ramps up the temperature until the temperature reaches the target temperature of the reaction mixture (Step S106).

By performing the first processing to the third processing, the temperature control unit conducts controlling such that a curve of temperature measurement values shows a trapezoidal waveform. At this time, it is desirable that each of the first processing of ramping down the temperature and the third processing of ramping up the temperature has a constant ramp rate.

Similar to the overshoot setting, the undershoot setting may be switched for each of the analysis items. For example, in a case of adopting a technique in which a target sequence is amplified by utilizing a primer, general spear-type undershooting can be employed for an analysis item having high specificity of reaction, and the temperature change speed of the reaction mixture can be improved. Meanwhile, in an analysis item in which nonspecific reaction is likely to occur when the temperature becomes lower than the target temperature, excessive cooling of the reaction mixture can be restrained and progress of the nonspecific reaction can be prevented by reducing the undershoot temperature range.

The undershoot setting may be handled by being combined with the pattern of the overshoot setting described above.

Hereinbefore, the methods of controlling overshooting and undershooting performed by the nucleic acid analyzer have been described. In a case where the nucleic acid analyzer having the plurality (in the present Example, 12 at the maximum) of the temperature control blocks 1 as illustrated in FIG. 2 can independently control the temperatures, differently set overshooting and undershooting can be respectively applied to the temperature control blocks 1. That is, in a case of performing an inspection of analysis items different from each other by using each of the temperature control blocks, optimal overshooting and undershoot setting can be applied to each of the analysis items.

The invention is not limited to the above-described Example and includes various modification examples. For example, the above-described Example has been described in detail in order to easily describe the invention and is not necessarily limited to a form having all of the configurations described above. In addition, a part of the configuration of a certain Example can be replaced by the configuration of a different Example. In addition, the configuration of a certain Example can be added to the configuration of a different Example. In addition, in regard to a part of the configuration of each Example, a different configuration can be added, deleted, and replaced.

In addition, in regard to each of the configurations, the functions, the processing unit, the processing means, and the like described above, a part or all thereof may be realized through hardware by designing an integrated circuit, for example. In addition, each of the configurations, the functions, and the like described above may be realized through software in which a processor interprets and executes a program realizing each of the functions. Information such as the program realizing each of the functions, a table, and a file can be placed in a recording device such as a memory, a hard disk, and a solid state drive (SSD).

In addition, a control cable and an information cable considered to be necessary in description are illustrated. All of the control cable and the information cable required in the product are not necessarily illustrated. Actually, almost all of the configurations may be considered to be connected to each other.

REFERENCE SIGNS LIST

1 TEMPERATURE CONTROL BLOCK
2 CAROUSEL
3 ROTARY AXIS
4 PELTIER DEVICE
5 TEMPERATURE SENSOR
6 PHOTOMETER
7 SHIELDING PLATE
8 WINDOW FOR IRRADIATION OF EXCITATION LIGHT
9 WINDOW FOR DETECTION OF FLUORESCENT LIGHT
10 TUBE
31 NUCLEIC ACID ANALYZER
32 TEMPERATURE CONTROLLER
33 APPARATUS CONTROLLER
34 INPUT DEVICE
35 DATA STORAGE/CALCULATION UNIT
36 DISPLAY DEVICE

The invention claimed is:

1. A nucleic acid analyzer comprising:
a carousel drivable around a rotary axis;
a plurality of holders disposed along an outer circumference of the carousel, each of the holders configured to hold a reaction vessel containing a sample obtained by mixing a reagent and a nucleic acid, each of the holders including an irradiation window and a detection window;
a Peltier device aligned radially with each of the holders and the carousel, each Peltier device sandwiched radially between a corresponding one of the holders and the carousel to control a temperature of said corresponding one of the holders;
a temperature sensor mounted to each of the holders;
a photometer disposed at an outer circumference of the carousel to supply excitation light to the irradiation window of each holder and to receive fluorescent light from the detection window;
each Peltier device, together with one of the holders and the temperature sensor mounted to said one of the holders, forming a temperature control unit, which controls a temperature of the sample;

an optical noise reducing shielding plate covering the carousel and the holders; and a temperature controller, which controls the temperature control unit, wherein during analysis of said sample, at sensed temperatures above a threshold value, the analyzer operates so that a curve of temperature values for duration time continuously ramps up the temperature values to a first target overshoot temperature, retains the first target overshoot temperature for a predetermined duration after reaching the first target overshoot temperature, then continuously ramps down the temperature values from the first target overshoot temperature to a reaction mixture target temperature, and thereafter maintains the reaction mixture target temperature, and so that, at sensed temperatures that are not above the threshold value, a curve of temperature values for duration time continuously ramps up the temperature values to a second target overshoot temperature lower than the first target overshoot temperature, and then continuously ramps down the temperature values from the second target overshoot temperature to the reaction mixture target temperature without retaining the second target overshoot temperature, and thereafter maintains the reaction mixture target temperature.

2. The nucleic acid analyzer according to claim 1, wherein the temperature controller has an input device through which a limit temperature range of overshooting or an upper limit value for a preset temperature in a PCR temperature cycle is input in advance.

3. The nucleic acid analyzer according to claim 1, wherein the temperature controller applies overshoot setting, which is configured to include two parameters of an overshoot temperature range and an overshoot duration time, to a preset temperature for each step in one cycle of a PCR temperature.

4. The nucleic acid analyzer according to claim 3, further comprising an input device through which a plurality of kinds of trapezoidal overshoot setting and threshold values for switching a parameter of trapezoidal overshooting are input to the temperature controller.

5. The nucleic acid analyzer according to claim 3, wherein the temperature control unit is one of a plurality of temperature control units, each of which independently controls a temperature.

* * * * *